US006814697B2

(12) United States Patent
Ouchi

(10) Patent No.: US 6,814,697 B2
(45) Date of Patent: Nov. 9, 2004

(54) ENDOSCOPE HAVING PROTECTIVE COVER FOR FLEXIBLE INSERTING TUBE

(75) Inventor: Teruo Ouchi, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/437,394

(22) Filed: May 14, 2003

(65) Prior Publication Data

US 2003/0216615 A1 Nov. 20, 2003

(30) Foreign Application Priority Data

May 16, 2002 (JP) ........................................ 2002-141014

(51) Int. Cl.$^7$ ................................................. A61B 1/04
(52) U.S. Cl. ....................................................... 600/121
(58) Field of Search ................................ 600/121, 122, 600/123, 124, 125, 139, 140, 144

(56) References Cited

U.S. PATENT DOCUMENTS 5,105,800 A * 4/1992 Takahashi et al. .......... 600/121
5,536,235 A * 7/1996 Yabe et al. ................. 600/121

FOREIGN PATENT DOCUMENTS

| JP | 61-24241 | 7/1986 |
| JP | 63-241 | 1/1988 |
| JP | 4-10807 | 2/1992 |
| JP | 5-44291 | 7/1993 |
| JP | 6-98115 | 12/1994 |
| JP | 2641789 | 5/1997 |
| JP | 3017574 | 12/1999 |

* cited by examiner

Primary Examiner—Beverly M. Flanagan
(74) Attorney, Agent, or Firm—Greenblum & Bernstein, P.L.C.

(57) ABSTRACT

An endoscope includes a flexible inserting tube to be inserted into a body cavity, an operation unit connected to a proximal end of the flexible inserting tube for operating the flexible inserting tube, and an hollow cylindrical cover member connected to the operation unit to surround a portion of the flexible inserting tube near the proximal end thereof. A proximal end portion of the cover member is made of a first material while a distal end portion thereof is made of a second material. The first material has higher stiffness than the second material.

15 Claims, 6 Drawing Sheets

ENDOSCOPE HAVING PROTECTIVE COVER FOR FLEXIBLE INSERTING TUBE

BACKGROUND OF THE INVENTION

The present invention relates to an endoscope having a protective cover that prevents a flexible inserting tube from being sharply bent in a vicinity of an end thereof connected to an operation unit.

A flexible inserting tube of an endoscope is connected, at a proximal end thereof, to an operation unit that is manipulated to control the bending of a bendable portion of the flexible inserting tube. Since the operation unit has a rigid body, buckling of optical fibers arranged within the flexible inserting tube is likely to occur if the flexible tube is sharply bent near the proximal end thereof connected to the operation unit. Therefore, some endoscopes are provided with an elastic protective cover that is connected to the operation unit so as to surround a proximal end portion of the flexible inserting tube and thereby prevent the flexible inserting tube from being bent sharply near the end connected to the operation unit.

The protective cover is a hollow cylinder having a tapered wall of which thickness increases toward the operation unit. Thus, the outer diameter of the protective cover is significantly larger at an proximal end thereof than at an distal end. Generally, such a configuration of the protective cover is suitable for an endoscope, specifically if the flexible inserting tube is much narrower compared to the operating unit, since a large step will not be formed between the flexible inserting tube and the operation unit.

Endoscopes provided with a disposal cover sheath are known. The cover sheath detachably covers the flexible inserting tube in order to prevent pollution of the flexible inserting tube during endoscopic inspections. The size of the cover sheath is adjusted to the size of the flexible inserting tube. A coupling ring is provided to the proximal end of the cover sheath. The flexible inserting tube is inserted into the cover sheath through the coupling ring until the coupling ring can be fixed to the operation unit.

The endoscope utilized together with the disposal cover sheath, however, cannot adopt the protective cover since the protective cover, of which the outer diameter considerably increases toward the proximal end thereof, inhibits the coupling ring to be moved to the operation unit and coupled thereto. Therefore, the flexible inserting tube of the endoscope provided with the cover sheath may easily bend near the end connected to the operation unit and causes buckling of the optical fibers arranged therein.

Therefore, there is a need for an endoscope provided with a protective cover that prevents sharp bending of a flexible inserting tube near the end thereof connected to an operation unit without inhibiting a coupling ring of a cover sheath to be coupled to the operation unit.

SUMMARY OF THE INVENTION

The present invention is advantageous in that an endoscope is provided that satisfies the above-mentioned need.

According to an aspect of the invention an endoscope is provided that includes a flexible inserting tube to be inserted into a body cavity, an operation unit connected to a proximal end of the flexible inserting tube for operating the flexible inserting tube, and an hollow cylindrical cover member connected to the operation unit to surround a portion of the flexible inserting tube near the proximal end thereof. A proximal end portion of the cover member is made of a first material while a distal end portion thereof is made of a second material. The first material has higher stiffness than the second material.

The endoscope arranged as above does not require significant increase of the wall thickness or the outer diameter of the cover member toward the proximal end thereof to get higher stiffness at the proximal end portion than at the distal end portion thereof. Thus, the cover member can be formed so as to have an outer diameter smaller than an inner diameter of a coupling ring of a cover sheath.

In an exemplary embodiment, the cover member includes a first member and a second member connected to a distal end of the first member. The cover member is connected to the operation unit at a proximal end of the first member. The first member is made of a material having higher resiliency than a material of the second member.

In the above case, each of the first and second members may have a tapered end, and connected to each other at the tapered ends thereof so that the stiffness gradually varies at a junction of the first and second members.

In another exemplary embodiment, the cover member includes a base cylinder and a stiffness adjusting cylinder. The base cylinder has a proximal side portion and a distal side portion having smaller outer diameter than the proximal side portion. The stiffness adjusting cylinder has lower stiffness than the base cylinder and is mounted on the distal side portion of the base cylinder. In this case, the thickness of the stiffness adjusting cylinder may be substantially equal to a half of an outer diameter difference between the proximal and distal side portions of the base cylinder, so that the outer diameter of the cover member becomes constant over the length thereof.

In still another embodiment, the cover member includes first, second, and third cylindrical members connected to each other in this turn, and the cover member is connected to the operation unit at a proximal end of the first cylindrical member. In this case, the first, second and third cylindrical members are arranged to have, respectively, highest, intermediate and lowest stiffness thereamong so that the stiffness of the cover member decreases from the proximal end toward the distal end thereof.

In still another embodiment, the cover member is made from a mixture of a first material and a second material having lower stiffness than the first material, and the rate of the first material in the mixture is decreased from a proximal end of the cover member toward a distal end thereof. In this case, the cover member may be further tapered such that wall thickness of the cover member decreases toward the distal end thereof.

According to another aspect of the invention, a protective cover to be connected to an operation unit of an endoscope for surrounding a flexible inserting tube connected at a proximal end thereof to the operation unit is provided. The cover member includes a hollow cylindrical body having a proximal end, a distal end, a proximal end portion defined in a vicinity of the proximal end, and a distal end portion defined in a vicinity of the distal end. The proximal end is formed to be connectable to the operation unit. The proximal and distal end portions are made of first and second materials, respectively. The first material has higher stiffness than the second material.

BRIEF DESCRIPTION OF THE ACCOMPANYING DRAWINGS

FIGS. 1A and 1B schematically show an endoscope and an cover sheath for the endoscope, respectively, according to an embodiment of the invention;

FIG. 2 shows a sectional view of a flexible inserting tube covered with the cover sheath according to the embodiment of the invention;

FIG. 3 schematically shows a part of the endoscope shown in FIG. 1A at which the flexible inserting tube is connected to an operation unit of the endoscope;

DETAILED DESCRIPTION OF THE EMBODIMENTS

Hereinafter, an embodiment of the invention will be described with reference to the accompanying drawings.

Figure 1A:
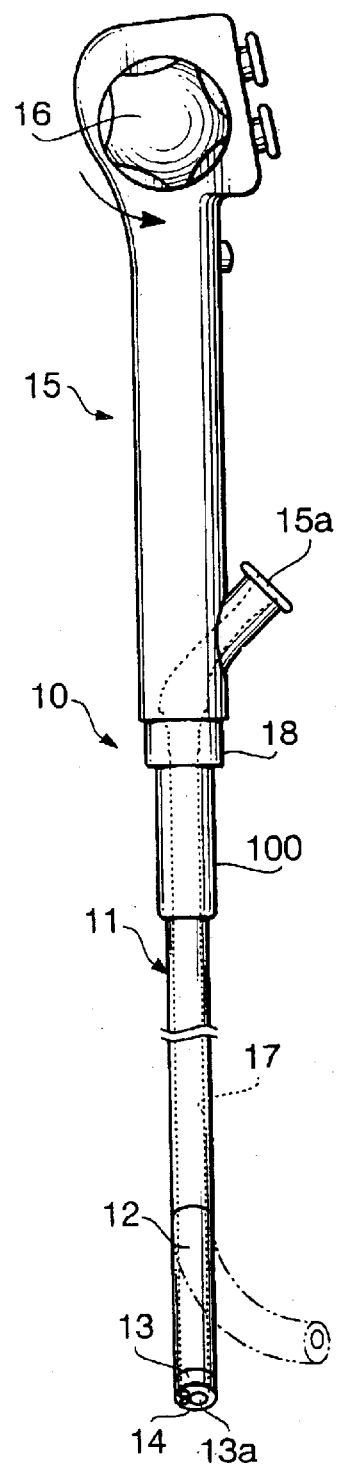
Figure 1B:
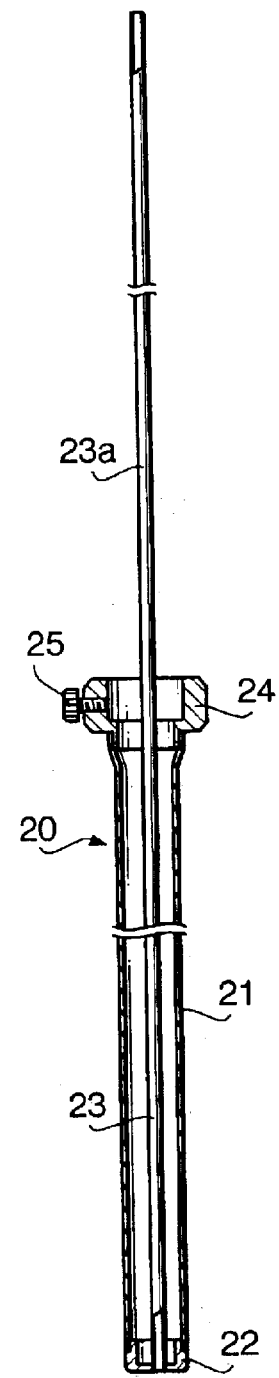

FIGS. 1A and 1B schematically show an endoscope 10 and an cover sheath 20 for an endoscope 10, respectively, according to the embodiment of the invention.

The endoscope 10 has an elongated flexible inserting tube 11 and an operation unit 15. A proximal end of the flexible inserting tube 11 is connected to the operation unit 15, and a distal end of the flexible inserting tube 11 is provided with a bendable portion 12, of which bending can be remotely controlled by manipulating a knob 16 provided to the operation unit 15. The bendable portion 12 bends as shown in chain double-dashed line in FIG. 1A when the knob 16 is turned. A tip body 13 provided with an observation window 14 is attached to a distal end of the bendable portion 12.

A hollow cylindrical protective cover 100 is connected to a distal end of the operation unit 15 so as to surround the flexible inserting tube 11 near the proximal end thereof, which is connected to the operation unit 15. The protective cover 100 is made of elastic material such as rubber, synthetic resin, or the like.

A guide channel 17 extends through the flexible inserting tube 11. The guide channel 17 is a flexible tube made of polyethylene resin, for example. One end of the guide channel 17 is connected to an opening 13a formed to the tip body 13, while the other end of the guide channel 17 is connected to an opening 15a formed to the operation unit 15.

The cover sheath 20 includes a cover tube 21, a cap member 22 and a coupling ring 24. The cover tube 21 is made of elastic material such as silicon rubber and has a thin wall. The inner diameter of the cover tube 21 is slightly larger than the outer diameter of the flexible inserting tube 11 so as to allow the flexible insertion tube 11 being smoothly inserted into the cover sheath 20. Further, the cover tube 21 is formed slightly shorter than the flexible inserting tube 11. Thus, the cover tube 21 have to be stretched to cover the whole flexible inserting tube 11, and when it is stretched, the diameter thereof reduces and the cover tube 21 comes into intimate contact with the outer circumferential surface of the flexible inserting tube 11.

The cap member 22 is attached to the distal end of the cover tube 21 in a water tight manner. The cap member 22 is a disk like member made of relatively hard and transparent material. The cap member is provided with a recess that receives the tip body 13 therein when the flexible inserting tube is inserted into the cover sheath 20.

The coupling ring 24 is fixed to the proximal end of the cover tube 21. The coupling ring 24 is formed in a shape and size such that a holding ring 18 of the operation unit 10, which will be describe later, can loosely fit therein. A screw 25 is provided at a side of the coupling ring 24. The screw is manually screwed in, when the coupling ring 24 receives the holding ring 18 therein, to press the holding ring 18 and thereby fix the coupling ring 24 thereto.

A treatment tool insertion channel 23, which is made of poly-tetra-fluoro-ethylene resin, is arranged within the cover tube 21.

The distal end of the treatment tool insertion channel 23 is connected to an opening formed to the cap member 22. Thus, a tool inserted through the treatment tool insertion channel 23 can protrude from the cap member 22.

The treatment tool insertion channel 23 is considerably longer than the cover sheath 20. Thus, the treatment tool insertion channel 23 extends throughout the cover sheath 20 and long beyond the coupling ring 24.

When the flexible inserting tube 11 is to be covered with the cover sheath 20, the treatment tool insertion channel 23 is passed through the guide channel 17 of the endoscope 10 by inserting the proximal end of the treatment tool insertion channel 23 into the guide channel 17 from the opening 13a of the tip body 13 and then pulling out from the opening 15a of the operation unit 15.

It should be noted that the treatment tool insertion channel 23 arranged as above can also be utilized as a suction channel.

Figure 2:
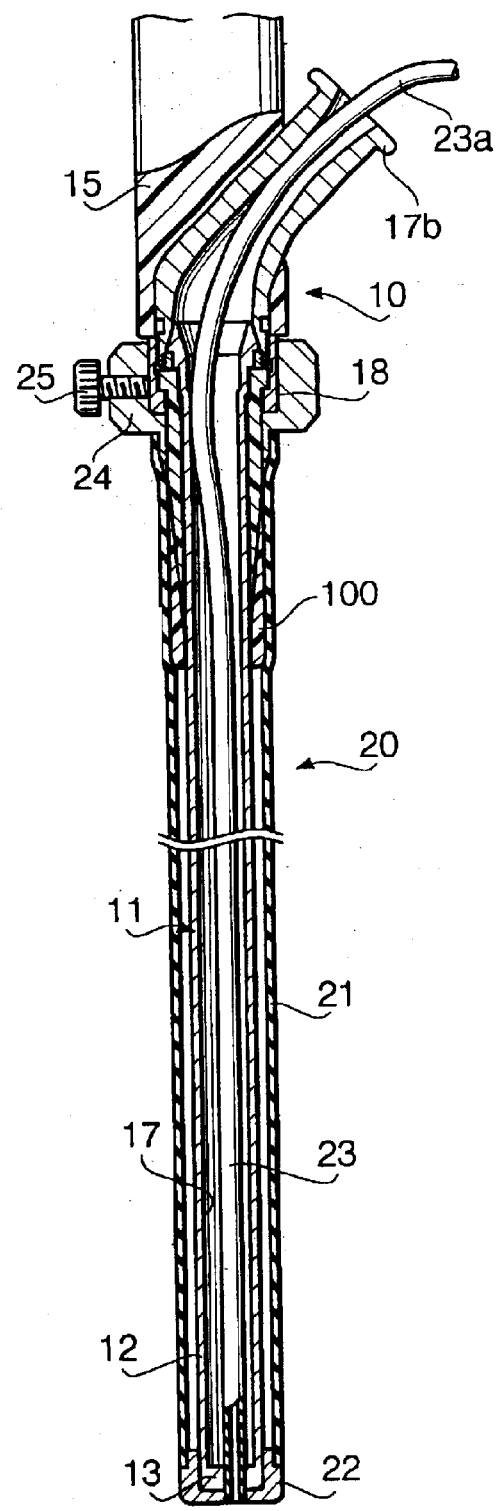

FIG. 2 shows a sectional view of the flexible inserting tube 11 covered with the cover sheath 20 according to the embodiment of the invention. In FIG. 2, the coupling ring 24 is fixed to the holding ring 18 of the operation unit 15 by tightening the screw 25. The cover tube 21 is stretched in the longitudinal direction thereof to bring the cap member 22 in intimate contact with the front surface of the tip body 13. In this state, the entire flexible inserting tube 11 and also the protective cover 100 are covered with the cover sheath 20. Thus, pollution of the flexible inserting tube 11 does not occur during the endoscopic inspection.

Figure 3:
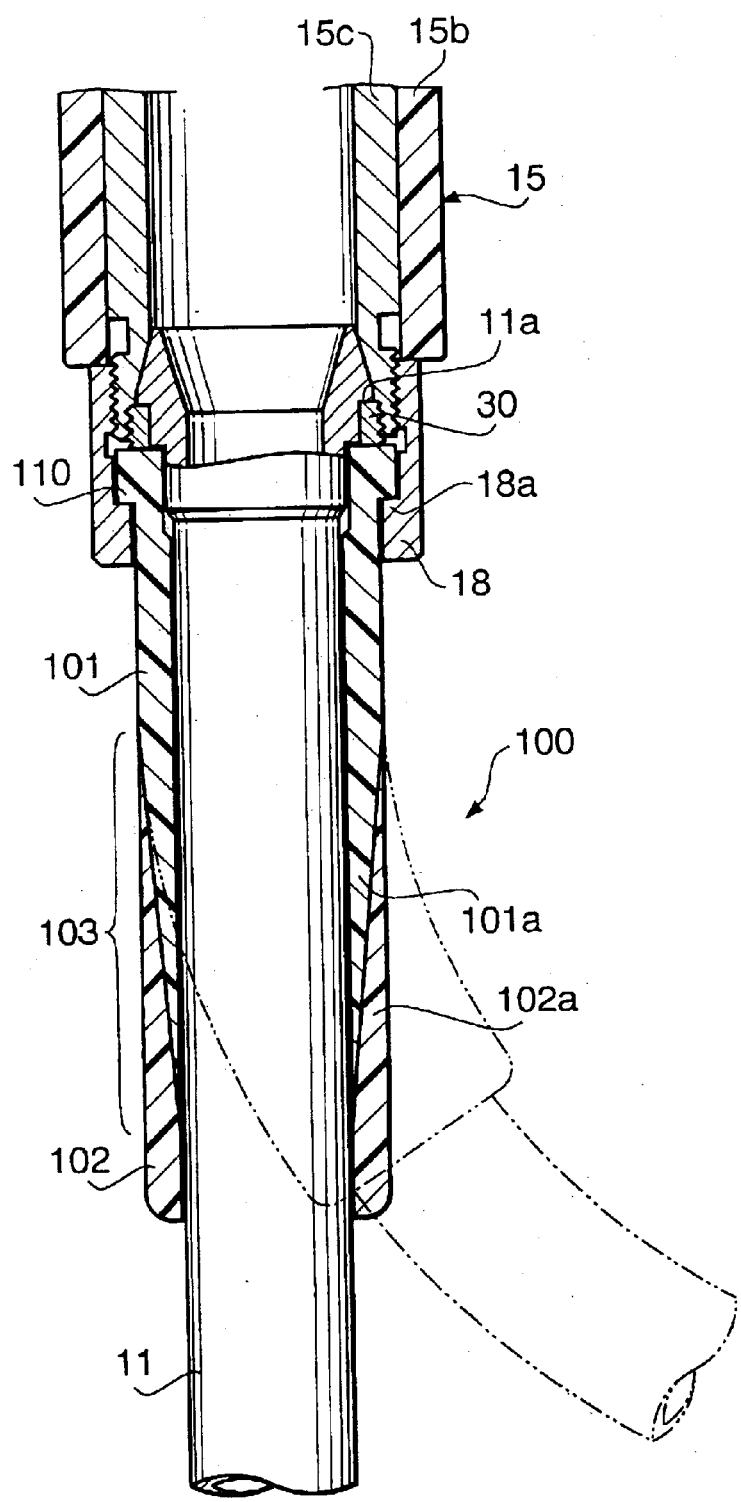

FIG. 3 schematically shows a part of the endoscope 10 at which the flexible inserting tube 11 is connected to the operation unit 15. Note that the operation unit 15 and the proximal end of the flexible inserting tube 11 are shown in sectional views. It should be also noted that optical fibers, various kinds of tubes and signal cables that are arranged within the endoscope are not shown in FIG. 3 for purpose of simplification.

The operation unit 15 has an outer body case 15b and an inner body case 15c which is fixed to the inside wall of the outer body case 15b. The inner body case 15c is arranged such that the distal end portion thereof protrudes from the outer body case 15b.

The proximal end of the flexible inserting tube 11 is placed within the distal end portion of the inner body case 15c. A flange 11a is formed around proximal end of the outer circumferential surface of the flexible inserting tube 11. The flange 11a abuts against a fixing ring 30 that is screwed into the distal end portion of the inner body case 15c. Thus, the proximal end of the flexible inserting tube 11 does not come off from the operation unit 15.

The protective cover 100 is a hollow cylindrical member having a constant wall thickness over the length thereof. A flange 110 is formed on the outer periphery of the proximal end of the protective cover 100. The flange 110 abuts against a circumferential protrusion 18a formed on the inner circumferential surface of the holding ring 18 screw coupled with the proximal end of the inner body case 15c. Thus, the protective cover 100 is prevented from dropping off from the operation unit 15 by the fixing ring 18. Note that the holding ring 18 screw coupled with the operation unit 15 serves also as a cover of the proximal end of the flexible inserting tube 11 connected to the operation unit 15.

The protective cover 100 includes a first portion 101 and a second portion 102 fixed to the distal end of the first portion 101. Both first and second portions 101, 102 are made of elastic material such as rubber (e.g., Urethane rubber, nitril rubber, or silicon rubber) or synthetic resin (e.g., soft polyurethane resin). Typically, the first and second portions 101, 102 are made of the same type of rubber or resin. The first portion 101 is made of rubber or resin being relatively hard or having relatively high resiliency (e.g., rubber having rubber hardness of 70 through 80 degree), while the second portion 102 is made of rubber or resin being more flexible or having less resiliency than that of the first portion 101 (e.g. rubber having rubber hardness of 30 through 50 degree). Thus, the protective cover 100 has a higher stiffness at the proximal side thereof than at the distal side. It should be noted that the protective cover configured as above is made, for example, by winding two pieces of rubber having different rubber hardness around a suitable rod and then carrying out the vulcanisation of those pieces of rubbers.

The first portion 101 has a tapered distal end 101a while the second portion 102 is provided with a tapered proximal end 102a. In other words, each of the distal end 101a of the first portion 101 and the proximal end 102a of the second portion 102 is formed such that the thickness thereof gradually varies in a direction parallel to a center axis of the protective cover 100. As shown in FIG. 3, the first and second portions 101 and 102 are connected to each other at the tapered ends thereof (101a, 102a) to form a junction 103. It should be noted that the wall thickness of the protective cover does not increases/decreases at the junction 103 but kept constant over the length thereof. Further, the stiffness and/or resiliency of the protective cover 100 gradually changes at the junction 103. That is, the protective cover 100 becomes gradually flexible from the proximal side to the distal side although the wall thickness, and hence the outer diameter, of the protective cover 100 is kept constant.

The protective cover 100 configured as above allows the flexible inserting tube 11 to bend with relatively small curvature at the proximal end of the protective cover 100 while preventing the flexible inserting tube 11 from bending sharply in the vicinity of the proximal end thereof. Therefore, buckling of optical fibers, which are placed within the flexible inserting tube 11, does not occur. It should be noted that the protective cover 100 achieves the above without increasing the wall thickness, and hence without increasing the outer diameter, thereof. Thus, the coupling ring 24 of the cover sheath 20 can be easily moved over the protective cover 100 and fixed to the holding ring 18.

Figure 4:
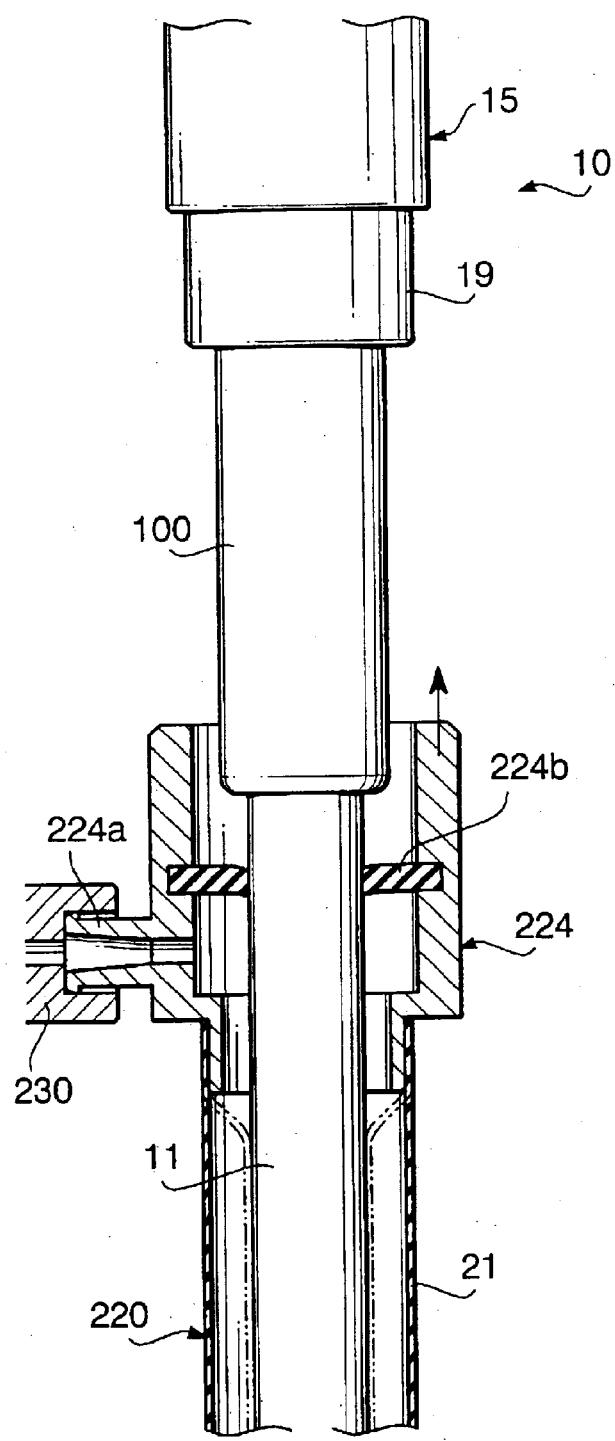
FIG. 4 shows a proximal end portion of a variation of the cover sheath shown in FIG. 1B.

FIG. 4 shows a proximal end portion of a variation of the cover sheath shown in FIG. 1B. Note that a part of the endoscope 10 is also shown in FIG. 4 with the flexible inserting tube 11 being partially inserted into the cover sheath 220. It should be also noted that in this and the following variations of the invention, elements that are substantially the same as those described in the embodiment above are denoted by the same reference numbers.

The cover sheath 220 shown in FIG. 4 has substantially the same configuration as the cover sheath 20 shown in FIG. 1B except that the coupling ring 24 is replaced with a modified coupling ring 224. Therefore, only the coupling ring 224 will be described hereinafter.

The coupling ring 224 differs from the coupling ring 24 in that it is provided with an air inlet 224a and a packing 224b. Except the above, the coupling ring 224 has the same arrangement as the coupling ring 24. Note that the screw 25 is not shown in FIG. 4 since it is located at the back side of the coupling ring 224.

The packing 224b is placed inside the coupling ring 224 and fixed to the inner wall thereof. The packing 224b has an annular shape. The flexible inserting tube 11 of the endoscope 10 is inserted into the cover sheath 20 through the annular packing 224b. The inner circumferential surface of the annular packing 224b make an air-tight contact with the outer circumferential surface of the flexible inserting tube 11 and/or the protective cover 100.

The air inlet 224a is formed to the side of the coupling ring 24. An air supplying tube 230 can be connected to the air inlet 224a to supply compressed air into the cover sheath 220 through the air inlet 224a. The compressed air supplied into the cover sheath 220 inflates the cover tube 21 and thereby facilitates the insertion of the flexible inserting tube 11 into the cover sheath 220.

Figure 5:
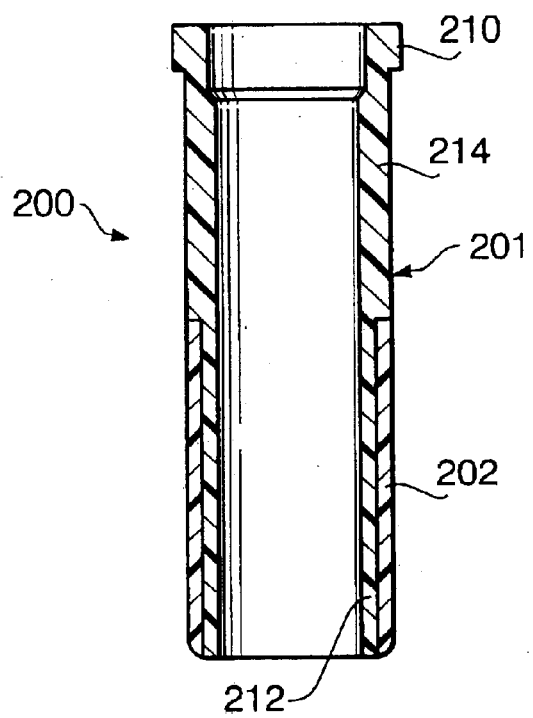
FIG. 5 shows a variation of an protective cover that can be used for the endoscope shown in FIG. 1A.

FIG. 5 shows a variation of the protective cover that can be used for the endoscope shown in FIG. 1A.

The protective cover 200 shown in FIG. 5 has a hollow cylindrical base member 201 and a hollow cylindrical stiffness adjusting member 202.

The base member 201 is provided with an outwardly extending flange 210 formed around the proximal end thereof. The flange 210 prevents the protective cover 200 from dropping off from the operating unit 15 by abutting against the fixing ring 30.

A distal side portion 212 of the base member 201 is formed as a small outer diameter portion 212 of which outer diameter is smaller than that of a proximal side portion 214 of the base member 201.

The stiffness adjusting member 202 is mounted to the base member 201 so as to cover the small outer diameter portion 212. The wall thickness of the stiffness adjusting member 202 is equal to the half of the outer diameter difference between the proximal and distal side portions of the base member 201. Thus, the wall thickness and/or the outer diameter of the protective cover 200 is substantially constant over the length thereof.

Both the base member 201 and the stiffness adjusting member 202 are made of elastic material such as rubber (e.g., Urethane rubber, nitril rubber, or silicon rubber) or synthetic resin (e.g., soft polyurethane resin). Typically, the base member 201 and the stiffness adjusting member 202 are made of the same type of rubber or resin. The stiffness adjusting member 202 is made of a material having lower stiffness than that of the base member 201. For example, the stiffness adjusting member 202 is made of rubber having rubber hardness of 30 through 50 degree, while the base member 201 is made of rubber having rubber hardness of 70 through 80 degree. Accordingly, the protective member 200 shown in FIG. 5 has higher stiffness at the proximal side thereof than at the distal side although the outer diameter thereof is substantially constant over the length thereof.

It should be noted that the stiffness adjusting member 202 may be formed to have an inner diameter smaller than the outer diameter of the base member 201 at the small outer diameter portion 212. In this case, the stiffness adjusting member 202 comes into close contact with the base member 201, due to the resiliency of the stiffness adjusting member 202, as the stiffness adjusting member 202 is mounted on the base member 201 and hardly slips off from the base member 201.

Figure 6:
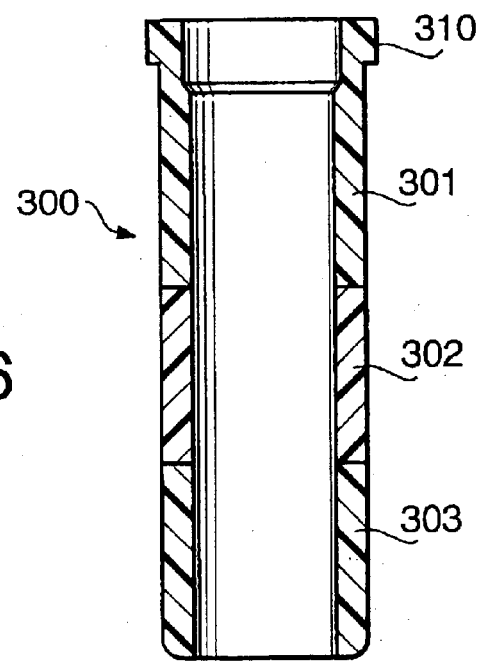
FIG. 6 shows another variation of the protective cover that can be used for the endoscope shown in FIG. 1A.

FIG. 6 shows another variation of the protective cover that can be used for the endoscope shown in FIG. 1A.

The protective cover 300 shown in FIG. 6 includes first, second, and third hollow cylindrical members 301, 302 and 303 connected to each other in this turn from the proximal side of the protective cover 300.

The first member 301 has a flange 310 formed at the proximal end of the outer circumferential surface thereof. The flange 310 abuts against the fixing ring 30 when the protective cover 300 is connected to the operation unit 15.

The first, second and third members have substantially the same length, the same outer diameter, and the same wall thickness. Thus, the protective cover 300 obtained by connecting the first through third members (301, 302, 303) has substantially a constant outer diameter and a constant wall thickness over the length thereof.

Each of the first, second and third members 301, 302 and 303 is made of elastic material such as rubber or synthetic resin. The material (or the stiffness and/or resiliency of the material) of each of the first through third members is selected such that the first, second and third members respectively have the highest, intermediate and the lowest stiffness thereamong. Accordingly, the stiffness of the protective member 300 shown in FIG. 6 decreases from the proximal side thereof toward the distal side although the outer diameter is substantially constant over the length. In the present embodiment, the first, second and third members 301, 302, 303 are made of soft polyurethane resin having hardness of 80°, 60° and 45°, respectively. The first through third members 301, 302, 303 can be connected to each other by welding, for example. Note that if the first through third members 301, 302, 303 are made of rubber, then they may be connected to each other by means of adhesive, or lining.

Figure 7:
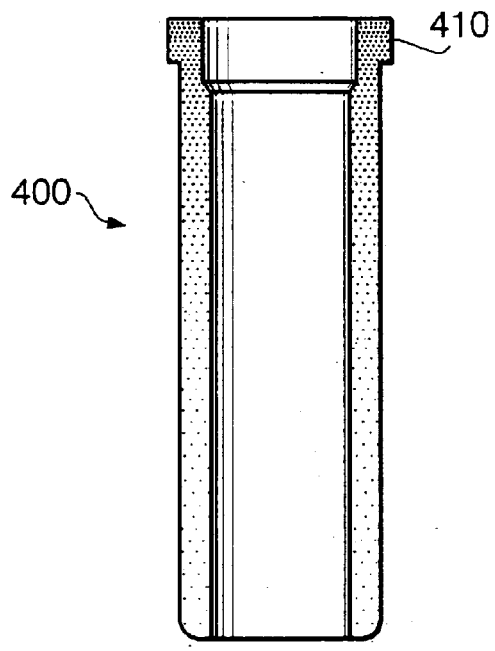
FIG. 7 shows still another variation of the protective cover that can be used for the endoscope shown in FIG. 1A.

FIG. 7 shows still another variation of the protective cover that can be used for the endoscope shown in FIG. 1A.

The protective cover 400 shown in FIG. 7 is a single hollow cylinder having a substantially constant outer diameter and wall thickness. A flange 410 is formed at the proximal end of the outer circumferential surface of the protective cover 400, which flange 410 has the same function as the flange 110 of the protective cover 100 shown in FIG. 3.

The protective cover 400 is made from a mixture of a first material and a second material. Both of the first and second materials may be rubber or elastic synthetic resin (e.g., soft polyurethane resin or soft vinyl chloride resin). The second material has lower stiffness or resiliency than the first material. The mixing ratio of the first and second materials is varied such that the stiffness of the protective cover 400 gradually decreases from the proximal end to the distal end thereof. In other words, the rate of the first material is decreased from the proximal end of the cover member 400 to the distal end thereof. Typically, the mixing ration of the first and second materials is changed such that the hardness of the protective cover 400 is 80° at the proximal end, 60° at the middle, and 45° at the distal end.

In the case the protective cover 400 is made of vinyl chloride resin, the protective cover 400 may be hardened by immersing the protective cover 400 into alcohol. With this regard, the protective cover 400 is immersed into alcohol longer at the proximal end thereof than at the distal end so that the stiffness of the protective cover 400 gradually changes from the proximal end toward the distal end.

Figure 8:
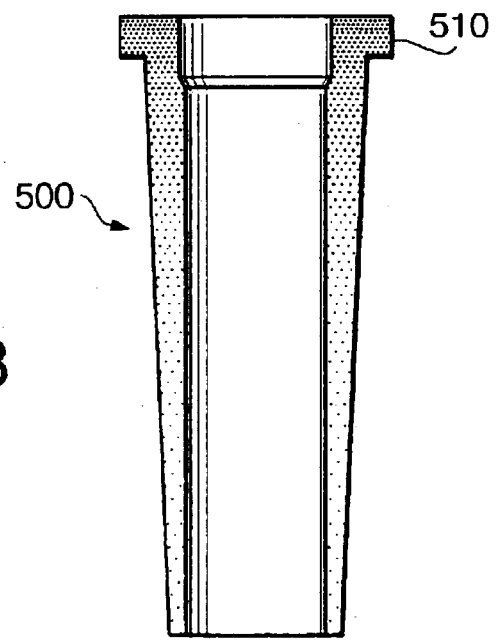
FIG. 8 shows a variation of the protective cover shown in FIG. 7.

FIG. 8 shows a variation of the protective cover shown in FIG. 7. The protective cover 500 shown in FIG. 8 is formed such that the wall thickness thereof gradually decreases toward the distal end thereof. Thus, the stiffness of the protective cover 500 is controlled not only by the material forming the protective cover 500 but also by the shape thereof such that the stiffness thereof is higher at the proximal end than at the distal end. It should be noted, however, the amount of wall thickness variation is kept within 30% of the average outer diameter of the protective cover 500.

The invention has been described in detail with particular reference to the embodiments thereof, but it will be understood that variations and modifications can be effected within the spirit and scope of the invention. For example, the protective covers described above may be utilized also for endoscopes that are not provided with a cover sheath.

The present disclosure relates to the subject matter contained in Japanese Patent Application No. P2002-141014, filed on May 16, 2002, which is expressly incorporated herein by reference in its entirety.

What is claimed is:

1. An endoscope, comprising:
    a flexible inserting tube configured to be inserted into a body cavity;
    an operation unit connected to a proximal end of said flexible inserting tube for operating said flexible inserting tube; and
    a hollow cylindrical cover member connected to said operation unit to surround a portion of said flexible inserting tube near said proximal end, a proximal end portion of said cover member being made of a first material, a distal end portion of said cover member being made of a second material, said first material having a higher degree of stiffness than said second material,
    wherein said cover member includes a first member and a second member connected to a distal end of said first member, said cover member being connected to said operation unit at a proximal end of said first member, said first member being of a material having a higher degree of resiliency than a material of said second member; and
    wherein each of said first and second members has a tapered end, said first and second members being connected to each other at said tapered ends.

2. The endoscope according to claim 1, further comprising a cover sheath that detachably covers said flexible inserting tube, said cover sheath including an elongated cover tube and a coupling ring connected to a proximal end of said cover tube, said coupling ring being detachably fixed to said operation unit when said flexible inserting tube is inserted into said cover tube through said coupling ring,
    wherein said cover member has an outer diameter smaller than an inner diameter of said coupling ring.

3. The endoscope according to claim 2, wherein said outer diameter of said cover member is substantially constant along a length of said cover member.

4. The endoscope according to claim 1, wherein said first and second members are of rubbers having different resiliencies from each other.

5. The endoscope according to claim 1, wherein said first and second members are of synthetic resins having different resiliencies from each other.

6. An endoscope, comprising:

a flexible inserting tube configured to be inserted into a body cavity;

an operation unit connected to a proximal end of said flexible inserting tube for operating said flexible inserting tube; and a hollow cylindrical cover member connected to said operation unit to surround a portion of said flexible inserting tube near said proximal end, a proximal end portion of said cover member being of a first material, a distal end portion of said cover member being made of a second material, said first material having a higher degree of stiffness than said second material, wherein said cover member includes a base cylinder and a stiffness adjusting cylinder, said base cylinder having a proximal side portion and a distal side portion having a smaller outer diameter than said proximal side portion, said stiffness adjusting cylinder being mounted on said distal side portion of said base cylinder, said stiffness adjusting cylinder having a lower degree of stiffness than said base cylinder.

7. The endoscope according to claim 6, wherein a thickness of said stiffness adjusting cylinder is substantially equal to a half of a difference in outer diameters between said proximal and distal side portions of said base cylinder.

8. The endoscope according to claim 6, further comprising a cover sheath that detachably covers said flexible inserting tube, said cover sheath including an elongated cover tube and a coupling ring connected to a proximal end of said cover tube, said coupling ring being detachably fixed to said operation unit when said flexible inserting tube is inserted into said cover tube through said coupling ring, wherein said cover member has an outer diameter smaller than an inner diameter of said coupling ring.

9. The endoscope according to claim 8, wherein said outer diameter of said cover member is substantially constant along a length of said cover member.

10. The endoscope according to claim 6, wherein said base cylinder and said stiffness adjusting cylinder are of rubbers having different resiliencies from each other.

11. The endoscope according to claim 6, wherein said base cylinder and said stiffness adjusting cylinder are of synthetic resins having different resiliencies from each other.

12. A protective cover configured to be connected to an operation unit of an endoscope for surrounding a flexible inserting tube connected at a proximal end thereof to the operation unit, the protective cover comprising, a hollow cylindrical body having a proximal end, a distal end, a proximal end portion defined in a vicinity of said proximal end, and a distal end portion defined in a vicinity of said distal end, said proximal end being configured to be connectable to said operation unit, said proximal and distal end portions being of first and second materials, respectively, said first material having a higher degree of stiffness than said second material, wherein said body includes a first member and a second member connected to a distal end of said first member, said first and second members being of said first and second materials, respectively, and wherein each of said first and second members has a tapered end, said first and second members being connected to each other at said tapered ends.

13. The protective cover according to claim 12, wherein said body has an outer diameter substantially constant along a length of said body.

14. A protective cover configured to be connected to an operation unit of an endoscope for surrounding a flexible inserting tube connected at a proximal end thereof to the operation unit, the protective cover comprising, a hollow cylindrical body having a proximal end, a distal end, a proximal end portion defined in a vicinity of said proximal end, and a distal end portion defined in a vicinity of said distal end, said proximal end being configured to be connectable to said operation unit, said proximal and distal end portions being of first and second materials, respectively, said first material having a higher degree of stiffness than said second material, wherein said body includes a base cylinder and a stiffness adjusting cylinder, said base cylinder having a proximal side portion and a distal side portion having a smaller outer diameter than said proximal side portion, said stiffness adjusting cylinder being mounted on said distal side portion of said base cylinder, said stiffness adjusting cylinder having a lower degree of stiffness than said base cylinder.

15. The protective cover according to claim 14, wherein said body has an outer diameter substantially constant along a length of said body.

* * * * *